(12) United States Patent
Roeper et al.

(10) Patent No.: US 6,591,126 B2
(45) Date of Patent: Jul. 8, 2003

(54) MICRODIALYSIS SYSTEM

(75) Inventors: Josef Roeper, Neuhofen (DE); Michael Schoemaker, Mannheim (DE); Christian Hoerauf, Oftersheim (DE)

(73) Assignee: Roche Diagnostics Corporation, Indianapolis, IN (US)

(*) Notice: Subject to any disclaimer, the term of this patent is extended or adjusted under 35 U.S.C. 154(b) by 0 days.

(21) Appl. No.: 09/910,452

(22) Filed: Jul. 20, 2001

(65) Prior Publication Data

US 2002/0082490 A1 Jun. 27, 2002

(30) Foreign Application Priority Data

Aug. 4, 2000 (DE) ......................................... 100 38 835

(51) Int. Cl.[7] ................................................. A61B 5/00
(52) U.S. Cl. ....................... 600/347; 600/352; 600/365; 600/366; 604/19
(58) Field of Search ................................ 600/345, 347, 600/352, 365, 366; 604/19

(56) References Cited

U.S. PATENT DOCUMENTS

| | | | | |
|---|---|---|---|---|
| 5,237,993 | A | * | 8/1993 | Skrabal ....................... 600/309 |
| 5,640,954 | A | | 6/1997 | Pfeiffer et al. ............... 128/635 |
| 6,190,316 | B1 | * | 2/2001 | Hirabayashi et al. ........ 250/281 |

FOREIGN PATENT DOCUMENTS

| | | |
|---|---|---|
| DE | 44 26 694 | 2/1996 |
| EP | 0 367 752 | 5/1990 |
| EP | 0 940 151 | 8/1999 |
| WO | WO 97/42868 | 5/1996 |

* cited by examiner

Primary Examiner—J. Casimer Jacyna
(74) Attorney, Agent, or Firm—Jill L. Woodburn; Richard T. Knauer

(57) ABSTRACT

The invention concerns a microdialysis system comprising a microdialysis probe (12) that can be inserted into organic tissue (10) and has a dialysis membrane (28) to separate a probe channel (18) filled with perfusion fluid from the tissue (10), a sensor cell (14) to determine the concentration of components and especially glucose in the perfusion fluid that is conveyed from the microdialysis probe (12) and a transport device (16) to convey the perfusion fluid through the probe channel (18) of the microdialysis probe (12) to the sensor cell (14). In order to enable a substantially pressureless transport of perfusion fluid through the microdialysis probe and thus to prevent undesired passage of fluid through the dialysis membrane (28), it is proposed that the transport device (16) has a pressure pump unit (30) connected on the pressure side to the inlet (20) of the probe channel (18) and a suction pump unit (31) connected on the suction side to the outlet (24) of the probe channel (18) that can be operated simultaneously with the pressure pump unit (30).

46 Claims, 1 Drawing Sheet

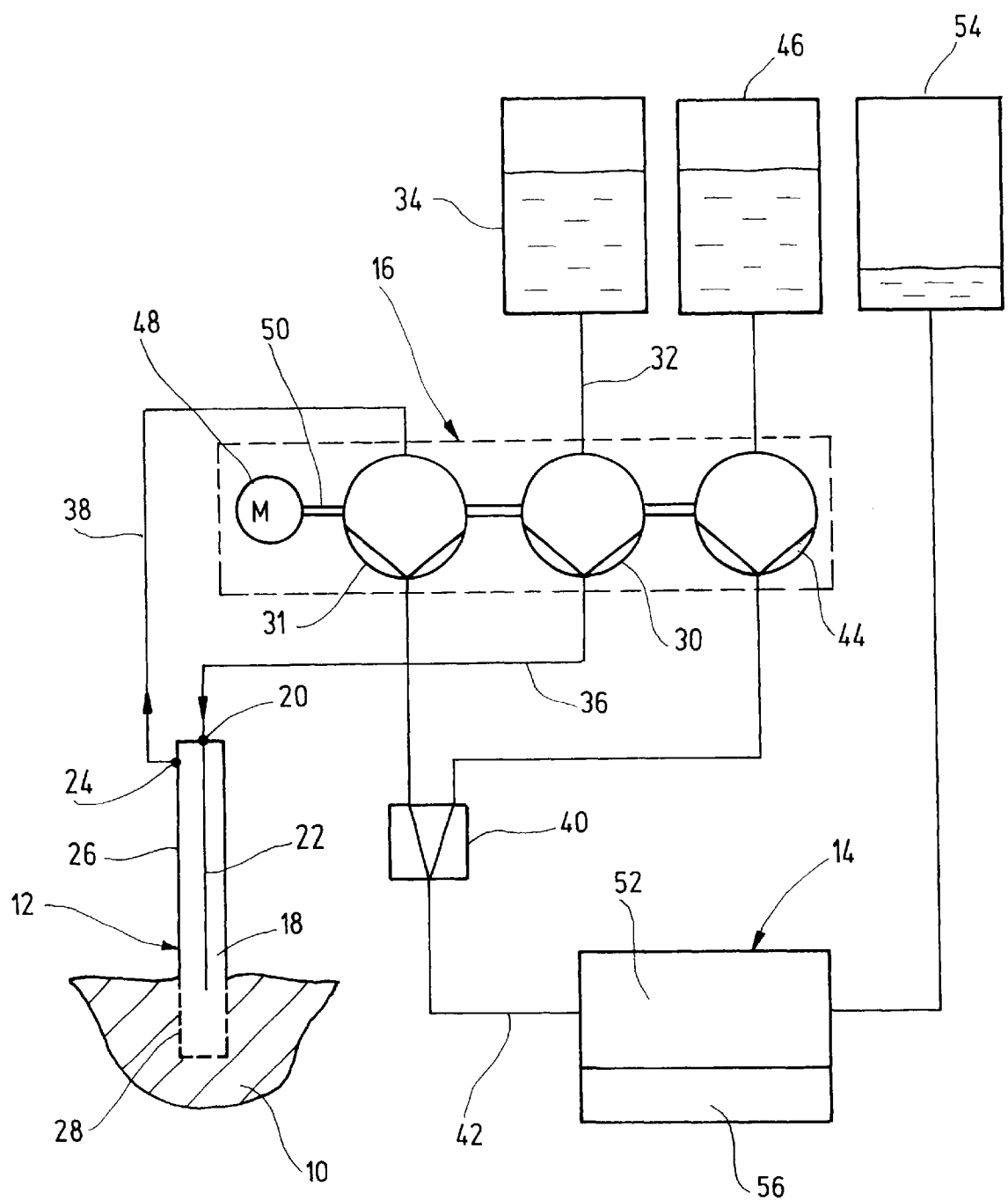

MICRODIALYSIS SYSTEM

BACKGROUND AND SUMMARY OF THE INVENTION

The invention concerns a microdialysis system comprising a microdialysis probe that can be inserted in organic tissue and has a dialysis membrane to separate a probe channel filled with perfusion fluid from the tissue, a sensor cell for the preferably electrochemical detection of components and especially glucose in the perfusion fluid that is conveyed from the microdialysis probe and a transport device to convey the perfusion fluid through the probe channel of the microdialysis probe to the sensor cell.

In a measuring system of this type known from WO 97/42868, the transport device has a dialysate pump downstream of the microdialysis probe embedded in the body tissue which sucks perfusion fluid from a reservoir through the probe and passes it on to the extracorporeal sensor cell while dialysate is formed. In this suction transport the operating pressure of the pump is adjusted according to the desired delivery rate to overcome the obstacles to flow in the suction branch. The small bore flow cross-sections thus result in a significant negative pressure difference (underpressure) of the perfusion fluid in the probe channel relative to the interstitial fluid. Consequently tissue fluid is practically sucked by ultrafiltration through the dialysis membrane into the probe. It has even been observed in in vitro experiments that the entire solution at the outlet of the probe is derived from ultrafiltration. Although in suction operation the actual flow rate of the dialysate solution leaving the microdialysis probe corresponds to the set value, the origin of the liquid (ultrafiltrate from body tissue or perfusate) is uncertain. Another disadvantage is that the function of the dialysis membrane can be impaired by a negative pressure gradient. In particular this can lead to a reduction of the active exchange surface by accumulation of macromolecules on the tissue side or by constructional factors and thus the amount of dialysate obtained is also reduced.

Conversely when the perfusion fluid is pressure fed by a perfusate pump in the delivery branch of the microdialysis probe, the problem arises that perfusion fluid, and hence essentially water, is discharged through the dialysis membrane into the tissue as a result of the required overpressure. This is disadvantageous since the tissue fluid around the probe is diluted, the tissue glucose has to diffuse into the probe channel against a counterflow of water molecules and the flow rate of perfusion fluid at the outlet cannot be determined due to the loss of liquid. A further disadvantage is that when the pump fails there is a risk that reagent solution added to the outlet branch can eventually pass into the body tissue via the microdialysis probe.

Based on this, the object of the invention is to eliminate the said disadvantages and to improve a microdialysis system of the type described above in such a manner that the dialysis function is reliable and defined.

A combination of features as stated in claim 1 is proposed as a solution to this object. Advantageous embodiments and further developments of the invention result from the dependent claims.

The essence of the invention is to utilize a combined push-pull transport of perfusion fluid to optimize the diffusion processes across the dialysis membrane. Accordingly the invention proposes that the transport device has a pressure pump unit which is connected on the pressure side with the inlet of the probe channel and a suction pump unit connected on the suction side with the outlet of the probe channel which operates simultaneously with the pressure pump unit. This allows a desired pressure level to be set in the region of the microdialysis membrane between the positive output pressure of the pressure pump unit and the negative input pressure of the suction pump unit. In this connection it is advantageous that the pressure pump unit is exclusively connected on the pressure side with the inlet and the suction pump unit is exclusively connected on the suction side with the outlet of the probe channel. This can be achieved by the pressure pump unit and the suction pump unit each being connected to the probe channel of the microdialysis probe by a non-branching duct which is preferably a flexible hose. This ensures defined flow conditions and guarantees that the mass flow through any flow cross-sections in the respective duct is of equal magnitude in the same time interval.

In a preferred embodiment the delivery rates of the pressure and suction pump unit are matched and are preferably essentially equal in order to reduce the effective pressure difference between the perfusion and tissue fluid across the dialysis membrane. This achieves an equilibrium at a low pressure level between the perfusion fluid and the tissue fluid across the dialysis membrane such that no ultrafiltration occurs and the origin of the solution which leaves the probe channel as well as its delivery rate and flow rate are known and defined. This also ensures that glucose passes through the dialysis membrane solely as a result of diffusion. At the same time this prevents the membrane from being sucked onto the probe lumen and thus maintains the effective membrane surface.

As a result of the push-pull operation it is possible to operate the dialysis process at low perfusion rates. The delivery rate of the pressure and suction pump unit is preferably less than 1 $\mu$l, preferably less than 0.1 $\mu$l per minute.

For long-term operation it is preferable that the suction side of the pressure pump unit is connected to a reservoir of perfusion fluid whereas the pressure side of the suction pump unit is connected to a flow chamber of the sensor cell which preferably terminates in a collecting vessel. The sensor cell or the sensor unit has an electrode arrangement operating electrochemically which allows a measuring signal to be detected in the flow chamber that correlates with the glucose content of the dialysate in a known manner. Basically it is also possible that the suction pump unit is downstream of the sensor cell so that the flow chamber is integrated in the suction path.

In order to chemically process the dialysate a reagent pump unit can be provided which is used to meter a reagent solution, in particular an enzyme solution, into the perfusion fluid upstream of the sensor cell. A further improvement, also with regard to reducing the risk of contamination, is achieved by connecting the pressure side of the reagent pump unit and of the suction pump unit preferably via a Y connector to a connecting duct leading to the sensor cell.

A technically advantageous embodiment of the system envisages that the pressure pump unit, the suction pump unit and optionally the reagent pump unit each consist of a flexible pump tube of a multichannel peristaltic pump that are actuated by a common rotating piston.

The microdialysis probe preferably comprises a double-lumen catheter which has a micropore dialysis membrane preferably made of hollow fibres in the area of its distal end, the outside of which is embedded in the tissue and the inside of which is filled with perfusion fluid.

BRIEF DESCRIPTION OF THE DRAWINGS

The invention is illustrated in more detail in the following by an application example which is shown schematically in the drawing. The single FIGURE shows a block diagram of a microdialysis system for determining the concentration of tissue glucose.

DETAILED DESCRIPTION OF THE INVENTION

The microdialysis system shown in the FIGURE is a measuring system that can be carried on the body of a patient which is essentially composed of a microdialysis probe 12 that can be inserted into the body tissue 10, a sensor cell 14 located downstream of the microdialysis probe and a transport device 16 for transporting perfusion fluid through the microdialysis probe 12 to the sensor cell 14.

The microdialysis probe 12 is a double-lumen catheter which forms a probe channel 18 through which flow can occur via an inlet 20 of the inner cannula 22 and an outlet 24 of the concentric outer cannula 26, the distal end of the inner cannula 22 communicating with the outer cannula 26. A dialysis membrane 28 made of hollow fibres is located in this area and separates the probe channel 18 from the surrounding tissue 10 and, as a result of its microscopic porosity, enables diffusion exchange of glucose between the tissue fluid and the perfusion fluid that passes through the probe channel 18 to obtain dialysate. Suitable microdialysis probes of this type are known in particular from DE-A 33 42 170 and U.S. Pat. No. 4,694,832 and can be obtained from the CMA/Microdialysis Company in Solna, Sweden under the name "CMA 60 Microdialysis Catheter" and "CMA 70 Brain Microdialysis Catheter".

For a combined pressure and suction feed of the perfusion fluid the transport device 16 has a pressure pump unit 30 and a suction pump unit 31. The suction side of the pressure pump unit 30 is connected via a feed tube 32 to a reservoir 34 containing a perfusion fluid such as a Ringer's solution and the pressure side is connected via a pressure line 36 to the inlet 20 of the probe channel 18. The suction side of the suction pump unit 31 is connected via a suction duct 38 to the outlet 24 of the probe channel 18 and on the pressure side feeds the aspirated perfusion fluid via a Y connecting piece into a connecting duct 42 which leads to the sensor cell 14. The connecting piece 40 enables a reagent solution to be added and in particular an enzyme solution for the enzymatically catalysed oxidation of the tissue glucose contained in the dialysate. For this purpose the transport device 16 has a reagent pump unit 44 which is connected on the suction side with a reagent solution reservoir 46 and on the pressure side with the second connection of the connecting piece 40. It is expedient that the pressure pump unit 30, the suction pump unit 31 and the reagent pump unit 44 each comprise one flexible pump tube of a single peristaltic pump such that the pump tubes can jointly be operated by means of a rotary piston 50 driven by motor 48. However, it is also basically possible to use sensors coated with immobilized enzymes (cf. DE-A-41 30 742) in which case, although it is possible to omit admixture of a reagent solution, drift problems may occur.

The connecting duct 42 ends in a flow chamber 52 of the sensor cell 14 the outlet of which is connected to a collecting vessel 54 for the perfusion fluid that passes through. The electrochemical sensor cell 14 has an electrode arrangement 56 which enters the flow chamber 52 and whose output signals can be transmitted to an evaluation unit, which is not shown, as a measure for the glucose content of the dialysate.

Details of the measuring and evaluation technology are for example known from DE 44 01 400 A1. Instead of an electrochemical measuring cell it is also conceivable to use detector units or optionally collecting units with a decentral sensor system based on a different measuring technology such as optical technologies.

The pump units 30, 31 are connected via the tubes 36, 38 directly i.e. without branching to the microdialysis probe 12. This enables a simultaneous pressure-suction operation by which means the perfusion fluid is transported while separately overcoming or specifically compensating for the flow resistances of the pressure duct 36 and the suction duct 38, the duct length being typically in the range of a few 10 cm and the inner diameter being 0.1 mm. Hence the perfusion fluid can be practically led, without the use of pressure, past the dialysis membrane 28 without a pressure gradient relative to the tissue fluid. For this purpose the delivery rates of the pump units 30, 31 and thus the input and output flow rates of the perfusion fluid are adjusted to the same value of for example 0.3 $\mu$l/min. This ensures that no undesired fluid passage through the dialysis membrane 28 occurs and that a defined adjustable amount of liquid per time unit flows through the microdialysis probe 12. In this manner mass transfer between the perfusion fluid and the tissue 10 surrounding the microdialysis probe 12 is essentially limited to diffusion processes and currents of fluid between the inner and outer space are largely avoided. If differences between the delivery rate of the pressure and suction pump cannot be completely avoided in a simple construction, it may be advantageous when the delivery rate of the pressure pump is slightly higher than the delivery rate of the suction pump to avoid undesired ultrafiltration.

What is claimed is:

1. Microdialysis system comprising
   a microdialysis probe (12) that can be inserted in organic tissue (10) and has a dialysis membrane (28) to separate a probe channel (18) from the tissue (10),
   a sensor cell (14) for the detection of components in the perfusion fluid that is conveyed from the microdialysis probe (12) and
   a transport device (16) to convey a perfusion fluid through the probe channel (18) of the microdialysis probe (12) to the sensor cell (14), characterized in that the transport device (16) has a pressure pump unit (30) connected on a pressure side to an inlet (20) of the probe channel (18) and a suction pump unit (31) having a suction side and being connected on the suction side to an outlet (24) of the probe channel (18) the suction pump unit operating simultaneously with the pressure pump unit (30).

2. Microdialysis system as claimed in claim 1, characterized in that the pressure side of the pressure pump unit (30) is exclusively connected to the inlet (20) and the suction side of the suction pump unit (31) is exclusively connected to the outlet (24) of the probe channel (18).

3. Microdialysis system as claimed in claim 1, characterized in that the pressure pump unit (30) and the suction pump unit (31) are each connected via a non-branching duct (36, 38) comprising a flexible tube, to the probe channel (18) of the microdialysis probe.

4. Microdialysis system as claimed in claim 1, characterized in that the delivery rates of the pressure and suction pump unit (30, 31) are matched in order to reduce the effective pressure difference across the dialysis membrane (28) between the perfusion and tissue fluid.

5. Microdialysis system as claimed in claim 1, characterized in that the delivery rates of the pressure and suction pump unit (30, 31) are essentially equal.

6. Microdialysis system as claimed in claim 1, characterized in that the delivery rate of the pressure pump unit (30) is larger by a predetermined amount than the delivery rate of the suction pump unit (31).

7. Microdialysis system as claimed in claim 1, characterized in that the delivery rate of the pressure and suction pump unit (30, 31) is less than 1 μl per minute.

8. Microdialysis system as claimed in claim 1, characterized in that the suction side of the pressure pump unit (30) is connected to a reservoir (34) for perfusion fluid.

9. Microdialysis system as claimed in claim 1, characterized in that the pressure side of the suction pump unit (31) is connected to a flow chamber (25) of the sensor cell (14) which terminates in a collecting vessel (54).

10. Microdialysis system as claimed in claim 1, characterized by a reagent pump unit (44) for metering a reagent solution into the perfusion fluid upstream of the sensor cell.

11. Microdialysis system as claimed in claim 10, characterized in that the pressure side of the reagent pump unit (44) and of the suction pump unit (31) are connected to a connecting duct (42) leading to the sensor cell (14).

12. Microdialysis system as claimed in claim 10, characterized in that the pressure pump unit (30), the suction pump unit (31) and the reagent pump unit (44) each comprise a flexible pump tube of a multichannel peristaltic pump actuated by a common rotary piston (50).

13. Microdialysis system as claimed in claim 1, characterized in that the delivery rate of the pressure and suction pump unit (30, 31) is less than 0.1 μl per minute.

14. Microdialysis system as claimed in claim 1, characterized in that the sensor cell is formed for the detection of glucose in the perfusion fluid.

15. Microdialysis system as claimed in one of the claims 1 to 12, characterized in that the microdialysis probe (12) comprises a double-lumen catheter (22, 26) which has in the area of the catheter's distal end the micropore dialysis membrane (28) formed from hollow fibres the outside of which is formed to be embedded in the tissue (10) and the inside of which is supplied with perfusion fluid.

16. A microdialysis system comprising
a microdialysis probe formed to be inserted in organic tissue to collect fluid from the tissue, the probe defining a probe channel having an inlet and an outlet and including a dialysis membrane, the dialysis membrane being formed to permit diffusion of fluid into the channel and to separate the probe channel from the surrounding tissue,
a sensor cell, and
a transport device formed to convey the fluid from the microdialysis probe to the sensor cell, the transport device including a pressure pump unit in communication with the inlet and a suction pump unit having a pressure side and a suction side and the suction side is in communication with the outlet, the pressure and suction pump units being formed to operate simultaneously with one another.

17. The system of claim 16 wherein the pressure pump unit includes a pressure side in communication with the inlet.

18. The system of claim 16 wherein the pressure side is in communication with the sensor cell.

19. The system of claim 17 wherein the sensor cell includes a flow chamber that terminates in a collecting vessel and the pressure side of the suction pump unit is in communication with the flow chamber.

20. The system of claim 16 further comprising a reservoir for perfusion fluid and wherein the pressure pump unit includes a suction side in communication with the reservoir.

21. The system of claim 16 wherein the pressure pump unit and the suction pump unit are each coupled via a non-branching duct to the probe channel.

22. The system of claim 21 wherein the duct is a flexible tube.

23. The system of claim 16 wherein pressure pump unit and the suction pump unit each include a delivery rate and the delivery rates are essentially equal.

24. The system of claim 16 wherein pressure pump unit and the suction pump unit each include a delivery rate and the delivery rate of the pressure pump unit is larger by a predetermined amount than the delivery rate of the suction pump unit.

25. The system of claim 16 wherein the pressure pump unit and the suction pump unit each include a delivery rate and the delivery rates are each less than 1 μl per minute.

26. The system of claim 25 wherein the delivery rates are each less than 0.1 μl per minute.

27. The system of claim 16 wherein the pressure pump unit and the suction pump unit each comprise a flexible pump tube of a multichannel peristaltic pump actuated by a common rotary piston.

28. The system of claim 16 wherein the microdialysis probe comprises a double-lumen catheter.

29. The system of claim 28 wherein the catheter has at an area of the catheter's distal end the micropore dialysis membrane.

30. The system of claim 29 wherein the membrane is formed of a hollow fibre.

31. The system of claim 30 wherein the outside of the fibre is formed to be embedded in the tissue and the inside of the fibre is formed to be supplied with the fluid.

32. A microdialysis system comprising
a microdialysis probe formed to be inserted in organic tissue to collect fluid from the tissue, the probe defining a probe channel having an inlet and an outlet and including a dialysis membrane, the dialysis membrane being formed to permit diffusion of fluid into the channel and to separate the probe channel from the surrounding tissue,
a sensor cell,
a transport device formed to convey the fluid from the microdialysis probe to the sensor cell, the transport device including a pressure pump unit in communication with the inlet and a suction pump unit in communication with the outlet, the pressure and suction pump units being formed to operate simultaneously with one another, and
a reagent pump unit formed to meter a reagent solution into the fluid upstream of the sensor cell.

33. The system of claim 32 wherein the reagent solution is an enzyme solution.

34. The system of claim 32 wherein the reagent pump unit and the suction pump unit are coupled to a duct leading to the sensor cell.

35. The system of claim 34 wherein the reagent pump unit includes a pressure side that is coupled to the duct.

36. The system of claim 34 wherein the duct is coupled to a Y-shaped connecting piece.

37. The system of claim 32 wherein the pressure pump unit, the suction pump unit, and the reagent pump unit each comprise a flexible pump tube of a multichannel peristaltic pump actuated by a common rotary piston.

38. A microdialysis system comprising
a microdialysis probe formed to be inserted in organic tissue to collect fluid from the tissue, the probe defining a probe channel having an inlet and an outlet and including a dialysis membrane, the dialysis membrane being formed to permit diffusion of fluid into the channel and to separate the probe channel from the surrounding tissue, a sensor cell including a flow chamber, a reservoir for perfusion fluid, and a transport device formed to convey the fluid from the microdialysis probe to the flow chamber of the sensor cell, the transport device including a pressure pump unit having a pressure side in communication with the inlet and a suction side in communication with the reservoir and a suction pump unit having a suction side in communication with the outlet and a pressure side in communication with the flow chamber of the sensor cell, the pressure and suction pump units being formed to operate simultaneously with one another.

39. The system of claim 38 wherein the pressure pump unit and the suction pump unit are each coupled via a non-branching duct to the probe channel.

40. The system of claim 38 wherein pressure pump unit and the suction pump unit each include a delivery rate and the delivery rates are essentially equal.

41. The system of claim 38 wherein pressure pump unit and the suction pump unit include a delivery rate and the delivery rate of the pressure pump unit is larger by a predetermined amount than the delivery rate of the suction pump unit.

42. The system of claim 38 wherein the pressure pump unit and the suction pump unit each include a delivery rate and the delivery rates are each less than 1 $\mu$l per minute.

43. A The system of claim 42 wherein the delivery rates are each less than 0.1 $\mu$l per minute.

44. The system of claim 38 further comprising a reagent pump unit formed to meter a reagent solution into the fluid upstream of the sensor cell.

45. The system of claim 44 wherein the pressure pump unit, the suction pump unit, and the reagent pump unit each comprise a flexible pump tube of a multichannel peristaltic pump actuated by a common rotary piston.

46. The system of claim 38 wherein the microdialysis probe comprises a double-lumen catheter.

* * * * *